United States Patent
Schneider et al.

(10) Patent No.: US 10,265,154 B2
(45) Date of Patent: Apr. 23, 2019

(54) IMPLANT FOR INFLUENCING THE BLOOD FLOW IN ARTERIOVENOUS DEFECTS

(75) Inventors: Manuel Schneider, Bochum (DE); Stefan Rolla, Bochum (DE); Carsten Aporta, Bochum (DE); Ralf Hannes, Dortmund (DE); Hermann Monstadt, Bochum (DE)

(73) Assignee: Phenox, GmbH, Bochum (DE)

( * ) Notice: Subject to any disclaimer, the term of this patent is extended or adjusted under 35 U.S.C. 154(b) by 0 days.

(21) Appl. No.: 13/821,350

(22) PCT Filed: Sep. 7, 2011

(86) PCT No.: PCT/EP2011/004498
§ 371 (c)(1),
(2), (4) Date: Apr. 17, 2013

(87) PCT Pub. No.: WO2012/031748
PCT Pub. Date: Mar. 15, 2012

(65) Prior Publication Data
US 2013/0211492 A1  Aug. 15, 2013

(30) Foreign Application Priority Data
Sep. 8, 2010 (DE) .................. 10 2010 044 746

(51) Int. Cl.
*A61F 2/06* (2013.01)
*A61F 2/90* (2013.01)
(Continued)

(52) U.S. Cl.
CPC .................. *A61F 2/06* (2013.01); *A61F 2/90* (2013.01); *A61F 2/95* (2013.01); *D04C 1/06* (2013.01);
(Continued)

(58) Field of Classification Search
CPC ...... A61F 2/06; A61F 2/95; A61F 2002/9505; A61F 2/90; A61F 2220/0025–2220/0091;
(Continued)

(56) References Cited

U.S. PATENT DOCUMENTS 4,441,215 A * 4/1984 Kaster .................... A61F 2/064
623/1.37
4,655,771 A * 4/1987 Wallsten .................. A61F 2/01
606/198

(Continued)

FOREIGN PATENT DOCUMENTS

DE 10127602 A1 12/2002
FR 2858208 A1 2/2005
(Continued)

*Primary Examiner* — Paul B Prebilic
(74) *Attorney, Agent, or Firm* — K. David Crockett, Esq.; Crockett & Crockett, PC

(57) ABSTRACT

A blood vessel implant to influence the flow of blood in the area of arteriovenous malformations. The implant has a wall of individual filaments forming a tubular braiding extending axially from the proximal to the distal end, the individual filaments crossing and forming points of intersection. The implant is deformable so that in an insertion catheter it is shaped so that its diameter is reduced and can be expanded at the implantation site adapting to the diameter of the blood vessel. The filament ends at the proximal and/or distal end of the braiding are each brought together at least in pairs and connected with each other permanently. The filament ends connect with each other and are shaped so as to be atraumatic The filaments cross at the points of intersection distally from the filament ends and are connected with each other at the proximal end of the implant.

11 Claims, 9 Drawing Sheets

(51) Int. Cl.
 A61F 2/95 (2013.01)
 D04C 1/06 (2006.01)
 A61F 2/966 (2013.01)

(52) U.S. Cl.
 CPC ........... *A61F 2002/9505* (2013.01); *A61F 2002/9665* (2013.01); *A61F 2220/005* (2013.01); *A61F 2220/0058* (2013.01); *A61F 2250/0043* (2013.01); *D10B 2509/06* (2013.01)

(58) Field of Classification Search
 CPC ........ A61F 2230/0069; A61F 2250/001; A61F 2250/0098
 See application file for complete search history.

(56) References Cited

U.S. PATENT DOCUMENTS

| | | | |
|---|---|---|---|
| 4,733,665 A * | 3/1988 | Palmaz | A61F 2/91 604/104 |
| 5,061,275 A * | 10/1991 | Wallsten et al. | 623/1.22 |
| 5,064,435 A * | 11/1991 | Porter | 623/23.7 |
| 5,405,377 A * | 4/1995 | Cragg | 623/1.2 |
| 5,476,508 A * | 12/1995 | Amstrup | 623/1.2 |
| 5,630,629 A * | 5/1997 | Moessinger | 285/133.4 |
| 5,630,829 A | 5/1997 | Lauterjung | |
| 6,083,257 A * | 7/2000 | Taylor | A61F 2/90 623/1.46 |
| 6,174,330 B1 * | 1/2001 | Stinson | A61B 17/12022 606/198 |
| 6,221,100 B1 * | 4/2001 | Strecker | A61F 2/90 623/1.22 |
| 6,264,689 B1 * | 7/2001 | Colgan et al. | 623/1.22 |
| 6,364,895 B1 * | 4/2002 | Greenhalgh | 606/200 |
| 9,034,026 B2 | 5/2015 | Hannes et al. | |
| 2001/0003801 A1 * | 6/2001 | Strecker | 623/1.11 |
| 2003/0040771 A1 * | 2/2003 | Hyodoh et al. | 606/200 |
| 2003/0149473 A1 * | 8/2003 | Chouinard et al. | 623/1.15 |
| 2005/0090893 A1 * | 4/2005 | Kavteladze et al. | 623/1.15 |
| 2005/0256563 A1 * | 11/2005 | Clerc et al. | 623/1.16 |
| 2006/0271097 A1 * | 11/2006 | Ramzipoor et al. | 606/200 |
| 2006/0276887 A1 * | 12/2006 | Brady | A61F 2/90 623/1.53 |
| 2007/0043432 A1 * | 2/2007 | Perouse | A61F 2/07 623/1.36 |

FOREIGN PATENT DOCUMENTS

| | | | |
|---|---|---|---|
| WO | 1997032546 A1 | 9/1997 | |
| WO | WO-97/32546 A1 * | 9/1997 | ............... A61F 2/06 |

\* cited by examiner

IMPLANT FOR INFLUENCING THE BLOOD FLOW IN ARTERIOVENOUS DEFECTS

The invention relates to an implant for blood vessels, in particular to influence the flow of blood in the area of arteriovenous malformations, said implant having a wall consisting of individual filaments forming, in essence, a tubular braiding extending in axial direction from the proximal to the distal end, wherein the individual filaments cross one another and form points of intersection, and wherein the implant being deformable in such a manner that, when accommodated in an insertion catheter, it is shaped so that its diameter is reduced and can be expanded at the implantation site adapting to the diameter of the blood vessel, and wherein the filament ends at the proximal and/or distal end of the braiding are each brought together at least in pairs and connected with each other permanently, and with the filament ends connected with each other being shaped so as to be atraumatic. The implant shall in particular serve to influence the flow of blood in the area of arteriovenous malformations, for example fistulas and aneurysms. It may also be used in the treatment of ischemic strokes, for example to restore, increase or maintain the blood flow. The implant may be designed so as to be recoverable.

Arteriovenous malformation may significantly impair a patient and may even result in fatal risks. In particular, this applies to arteriovenous fistulas and aneurysms, especially when these are found to exist in the cerebral region. Normally, attempts are made to close off such malformations by implants which, as a rule, are placed in position by endovascular techniques with the help of catheters. Especially when treating aneurysms implanting platinum spirals has proven its worth, said spirals fill the aneurysm more or less completely, largely obstruct the blood inflow and enable a local thrombus or clot to form which fills and ultimately closes off the aneurysm. Nevertheless, this treatment approach only suits aneurysms that have a relatively narrow access to the vessel system, so-called aciniform aneurysms. In the event of vessel protuberances having a wide access to the blood vessel there is a risk that the implanted spirals may become flushed out and cause damage to other areas of the vascular system.

In such cases it has already been proposed to place into position a kind of stent that "bars" the opening of the aneurysm and in this way prevents the occlusion spirals from being flushed out. Stents of this nature that are provided with a wide-meshed wall have certain drawbacks, however.

On the one hand, this concerns the wide-meshed structure which does not prevent blood from entering the aneurysm. So if the occlusion means does not occupy the aneurysm space adequately the pressure exerted on the vessel wall persists unabated. An aftertreatment in this case may be difficult, however, because the stent will obstruct access to the aneurysm and impair the placement of additional occlusion means.

Another drawback is that the stent cannot be adapted to its placement site. In the interest of functioning optimally the stent should have close contact with the vessel wall but not exert excessive pressure on the wall. Other than stents serving the purpose of expanding vessels to counteract stenoses this type of stent must rather be viewed as a kind of sleeve the influence of which on the vessel lumen and endothelium wall of the vessel shall be as slight as possible. It thus follows that this stent type is only of limited use when it comes to meet the respective requirements even if it has been selected especially for the envisaged purpose.

Stents consisting of wire braiding are known for a long time, particularly for applications in the coronary area. These stents are usually manufactured as a round braiding structure with the individual wire filaments forming the stent wall in layers of oppositely running spirally or helically shaped elements. In this way a mesh braiding is produced that both supports in radial direction and is permeable to blood.

A problem encountered with these stents of circular braiding design is that on the free ends the small-diameter loose ends may have traumatic effects.

As proposed by U.S. Pat. No. 4,655,771 (Wallsten) such a stent of circular braiding is provided in its terminal areas with U-shaped connecting links arranged between the loose ends which makes it atraumatic. However, the U-shaped connecting links are prone to cause stresses and thus lead to deformation of the stent.

As per U.S. Pat. No. 5,061,275 (Wallsten et al.) the loose ends of such wire stents are rounded off by laser treatment to counteract traumatization. The stent proposed in that publication also consists of circular braiding the individual wires of which are provided with impressions in the knots area so as to enable a stress-free fixation within the wall structure.

Such stents of circular braiding design consisting of filaments are, when used for the treatment of stenoses, expanded hydraulically by means of balloons at the placement site and attached to the vessel wall. During placement the balloon attached to a pusher wire serves as transportation element over which the stent is crimp-mounted. However, such a transportation element should not be used for implants intended to influence or channel the flow of blood in the cerebral region; on the contrary, an implant automatically adapting to the vessel diameter and leaning against the vessel wall is of advantage in this case.

Another problematic aspect associated with stents or implants made of wire braiding is their manufacture. Manufacturing them in the form of a braided endless hosing cut off to the desired length is viewed beneficial. In this case loose wire ends are produced at the two ends of the cut-to-size hosing which must be made blunt at great expense, for example by providing for the attachment of the above mentioned connecting links.

Publication WO 2008/107172 A1 describes an implant the braiding of which has an elongated shape of reduced diameter within an insertion catheter and expands at the placement site thus adapting to the vessel diameter and increasing its braiding density, wherein the filament ends projecting at the implant ends are brought together at least in pairs and connected with each other. In this manner an implant was provided that was capable of adapting to the relevant vessel diameter and had atraumatically designed filament ends.

From DE 10 2009 006 180 A1 an implant is known that also aims at achieving atraumatic properties. This publication proposes that the wire ends are joined to form first braiding ends which in turn are joined to form second braiding ends.

However, with all these implants a problem was encountered in that upon liberation of the implant the filament ends at the proximal end do not widen sufficiently towards the vessel walls sometimes. This effect is also occasionally referred to in literature as "fish mouth effect" and, among other reasons, is due to the fact that the radial forces acting at the proximal end of the implant are lower than at the distal end. When the implant is released the cover arranged above the implant is removed first resulting in the distal end being free to expand whereas the proximal end continues to be connected to the detachment mechanism. Only when the detachment mechanism has been separated will the proximal end be free to expand as well. However, the forces causing the proximal end to move outwards are lower here than at the distal end and in the central area because expansion in this case must take place unaided, i.e. without additional support.

The fish mouth effect results in the filament ends at the proximal end projecting into the vessel lumen and thus interfering with the flow of blood. Consequently, this may even jeopardize and render inadequate the implant's atraumatic properties. Further interventions, for instance involving a catheter to be moved past the implant, are more difficult or impaired.

It is thus the objective of the present invention to provide an implant of the kind first mentioned above wherein the radial expansion of the implant is ensured at the proximal end.

This objective is accomplished by the invention proposing an implant for blood vessels, in particular to influence the flow of blood in the area of arteriovenous malformations, said implant having a wall consisting of individual filaments forming, in essence, a tubular braiding extending in axial direction from the proximal to the distal end, wherein the individual filaments cross one another and form points of intersection, and wherein the implant being deformable in such a manner that, when accommodated in an insertion catheter, it is shaped so that its diameter is reduced and can be expanded at the implantation site adapting to the diameter of the blood vessel, and wherein the filament ends at the proximal and/or distal end of the braiding are each brought together at least in pairs and connected with each other permanently, and with the filament ends connected with each other being shaped so as to be atraumatic, and wherein the filaments crossing one another at the points of intersection located distally from the filament ends are directly or indirectly connected with each other at the proximal end of the implant.

It has been found that by a fixation of the filaments to each other in the area of the intersections at the proximal end the implant will be capable of sufficiently expanding radially also at this end resulting in the ends of the filaments to be in close contact with the vessel wall. The insufficient radial expansion of the filaments of the described prior-art implants is, inter alia, considered to be due to the fact that friction occurs at the points of intersection between the filaments, said friction impeding the expansion process. This friction is eliminated by the fixation of the filaments with respect to each other in the area of the intersections. The points of intersection are thus held in a certain axial position relative to the proximal end of the implant so that a displacement of individual intersecting points is ruled out which may otherwise cause interference between filaments when expansion occurs.

By the term points of intersection or intersections at the proximal end of the implant intersections are to be understood where the filaments cross each other but not the filament ends themselves, i.e. the point where the filaments are connected to each other permanently. The proximally arranged points of intersection are therefore located marginally in distal direction when facing the proximal end of the filaments. In accordance with the invention, when referring to the points of intersection at the proximal end of the implant, those points of intersection are to be understood that are located orthogonally to the longitudinal direction of the implant within the first three intersection levels, i.e. the points of intersection arranged farthest to proximal, the second-farthest proximal intersections and the third-farthest proximal intersections. Preferably connected with one another are at least filaments crossing each other at the intersections located farthest to proximal but it may also be expedient to connect crossing filaments located at points of intersection arranged somewhat farther to distal. Also conceivable is a connection of filaments crossing each other at points of intersection in the distal area of the implant.

The attachment of the filaments to each other at the proximally located points of intersection can be realized by various methods. One possible method is to pass the filaments through loops formed by separate wires. These wires are secured to the implant, preferably at the proximal end of the implant. The filaments crossing at the points of intersection are run through loops so that the intersection is to a great extent held in its axial position preventing the filaments from sliding past each other and resulting in friction between the filaments to be ruled out. On the other hand, freedom of movement, though greatly restricted, between the individual filaments still exists so that the expansion of the implant is not impaired.

The wires forming the loops may in particular originate from the points where the filaments are brought together at the proximal end. The connection may be brought about, for example, by means of laser welding, brazing, adhesive bonding or the like. The individual wires extend from the proximal point of attachment in distal direction and are passed around the proximal points of intersection of the filaments.

Alternatively, at least some of the filaments may themselves form eyelets at the intersections located farthest to proximal through which in each case one or several other filaments are run that cross with the eyelet-forming filament at this point of intersection. Such other filament may itself be provided with an eyelet in this location to appropriately hold the filaments in position. With this embodiment no separate wire for the fixation of the filaments will be needed.

Further alternative configurations are conceivable by means of which the filaments can be connected in the area of the proximal intersections. In particular, the filaments may thus be knotted together or bonded, soldered or welded together at this point. Other form-closing or otherwise firmly bonded connection types are conceivable as well. Nevertheless, the connection should offer a certain degree of flexibility so that changes in the angle at which the filaments cross at the points of intersection can still take place.

The inventive tubular braiding is in most cases of round shape and has a circular cross section when facing its proximal or distal end. However, the braid may also have a shape other than circular, for example an oval cross section may be provided.

Single wires made of metal may be employed as filaments forming the braiding structure but it is also possible to use strands, i.e. several wires of small diameter arranged so as to form a filament, preferably twisted around each other.

The implants according to the invention are capable of influencing the flow of blood in a vessel in such a way that arteriovenous malformations are sealed off from the blood flow to the extent possible. The same applies to the occlusion of vessels which, for example, are to be separated from the blood circulation system, e.g. because they feed blood to tumors. By appropriately selecting the implant diameter to suit the respective vessel diameter the implant should then be capable of adapting to the relevant vessel diameter. In the area of enlargements and protuberances it shall expand to its nominal diameter.

Moreover, the implant is capable of being placed in an atraumatic manner, i.e. without the help of a balloon. A placement device must reliably retain the implant until it is finally released from the catheter and, in particular, should also enable the implant to be retracted into the catheter in the event it has not yet been released completely.

Suitable materials for the inventive implant are, in particular, those that have a high restoring force or spring action. These are especially materials having superelastic or shape-memory properties, for example nitinol. To form the individual filaments wires of different diameter may also be used. Wires of greater diameter in this case ensure that radial strength is sufficient whereas wires of smaller diameter bring about an adequately high mesh density. Such a design makes it possible to combine or counterbalance the advantages and drawbacks associated with wires of different cross sections. In most cases the wire cross section is round but wires having oval or square cross sections or combinations thereof may also be employed.

In the framework of the description the term proximal end denotes the end situated nearest to the attending physician, meaning the proximal end points into the direction outside of the body. Vice versa, the distal end faces away from the physician, i.e. points towards the inside of the body. Accordingly, proximal and distal are to be understood as being nearest to or furthest away from the pusher wire of the placement system.

The implants according to the invention are described by reference to a braid intended to seal off of an aneurysm. It is to be understood that braidings of this type may serve a variety of purposes, in particular for the treatment of other types of arteriovenous malformations.

The implants according to the invention must not necessarily have a supporting function as is the case with customary stents. Primarily, they rather serve to channel the flow of blood in the area of the malformations. For example, they shall prevent occlusion means placed in an aneurysm from being flushed out into the vascular pathway. Moreover, the inflow and/or outflow of blood in an aneurysm can be prevented. It is to be viewed rather as a kind of in-line element, internal sleeve or flow diverter. Basically however, the inventive implants may also serve to perform the supporting function the customary stents are fulfilling.

The implants according to the invention are manufactured as braiding consisting of a multitude of filaments, wherein the braid basically forming an endless hose. This endless hose can then be cut to the length desired for the relevant implant. The individual filaments are wound spirally or in the form of a helix, with the individual filaments being intertwined to form a braiding, i.e. crossing one below and above the other. For this purpose, the individual filaments are as a rule wound in two directions thus crossing each other at a constant angle, with this angle of intersection being, for example, 90°. According to the invention—and in normal stress-free condition—angles of more than 90° are preferable, especially those ranging between 90 and 160°; and the angles meant here are those which are open towards the axial ends of the implant. Provided it is sufficiently dense, such a steep winding of the individual filaments can produce a braiding of high surface density capable of being stretched in axial direction thus yielding significantly smaller diameters. If the stretching forces are omitted and the restoring force of the filament material is sufficiently high the braiding again approaches its nominal diameter, i.e. the originally existing stress-free condition, and expands which at the placement site leads to a close contact with the vessel wall and causes the mesh structure at the wall to become denser. In particular, this also applies to areas where vessel enlargements exist. In addition, the surface density of the braid can also be varied by the braiding technique used. In the center area for example where aneurysms are typically closed off the braided structure of the implant may be denser than in its end regions which ensures the neck of the aneurysm is covered to a great extent. On the other hand, if the surface density in the end regions is reduced this will yield adequate flexibility.

In the inventive braid the filament ends protruding from the ends of the implant are joined at least in pairs and connected with each other permanently. This may, for example, be achieved by welding or by a mechanical clasping method, twisting, soldering, or adhesive bonding. A connection of the filament ends may also be achieved by means of a mounted sleeve. Such a sleeve may be firmly bonded to the filament ends, for example it may be connected by welding or also by crimping. As an alternative the sleeve may be suitably sized such that thicker slubs or nubs arranged at the ends of the filaments are prevented from passing or sliding through said sleeve. The sleeve is thus slidable in axial direction relative to the filaments but cannot be completely pulled off. It is moreover considered advantageous if the sleeves are of staggered arrangement in axial direction. Such an arrangement will ensure that the sleeves are not positioned one over the other when the implant is compressed so that a smaller overall implant diameter can be achieved.

Also conceivable is to bring the filament ends together to form first braiding ends which in turn are joined to form second braiding ends, as has been described in DE 10 2009 006 180 A1.

Another optional arrangement provides for the filament ends to be formed into loops, i.e. the filament ends at the proximal/distal ends are brought together and bent back by 180° which renders them atraumatic. The filament ends can be secured by slipped-on sleeves or capped-on coils. The connection is made by crimping, adhesive bonding or similar method.

During this process or additionally the joined filament ends are formed such that they do not cause traumatic effects. In particular, the filament ends may be provided distally and proximally with an atraumatic thicker element of roughly spherical or ball shape for example. Such slubs/thickenings may be shaped out of the filament end or attached to it by laser welding, brazing, adhesive bonding, crimping or similar methods.

In actual practice placement of the inventive implants will be under radiographic control. The implant should therefore be provided with a radiopaque marker material or entirely consist of a radiopaque material. Such radiopaque materials are in particular tantalum, gold, tungsten, and platinum metals, for example Pt—Ir alloys, with the latter to be given preference. These markers may, for instance, be attached as marker elements to the ends of the filaments in a manner known per se or plaited into the braid structure of the implant as marker filaments. Individual filaments may as well be sheathed in a helix or enclosed in wire consisting of radiopaque material such as platinum. The helix or wire may be attached to the filaments by welding, adhesive bonding or the like. It is also possible to coat or fill the filaments with a radiopaque material.

Another alternative approach are radiopaque markers in the form of sleeves surrounding the joined filaments. These sleeves may also be welded to or crimped onto the ends of the filaments. The radiopaque sleeves may be identical to the sleeves bringing the filament ends together as mentioned hereinbefore and thus fulfill a dual function.

The inventive implants as a rule are not hydraulically expanded and placed in position by means of a balloon. Nonetheless it is necessary to connect the implants to a pusher wire in such a manner that they can be reliably controlled. As proposed by the invention this is achieved via connecting elements interacting with a retaining element of the pusher wire needed for the placement process. Such connecting elements may be the braiding's filament ends combined with each other.

Vessel branches (bifurcations) can be taken into account with the inventive implants, for example, in that areas of lower mesh density are provided.

Basically, the braiding may be plaited in any known way. It may have a one-plaited and/or multi-plaited structure. Especially when used in a narrowly plaited arrangement a dense braiding will cause the individual filaments to be highly stressed. However, while a multi-plaited design is conducive to removing stresses from the braid, a too highly plaited arrangement on the other hand will cause the bond in the braid to deteriorate. The plaiting method indicates how many times a given filament passes crossing filaments on the same side of such filaments before it changes sides and subsequently passes on the other side of a corresponding number of crossing filaments. In case of a two-plaited arrangement a filament, for example, passes in succession over two crossing filaments and then in succession along the underside of two crossing filaments.

In particular, also multi-ply filaments may employed. The plying indicates the number of joined, parallelly arranged individual filaments. Single or multiple plying may be provided with one or several individual filaments extending in parallel. Since during the braid manufacturing process filaments are introduced into the process from bobbins, one or several individual filaments are fed from the respective bobbin simultaneously to the mandrel on which the braiding is produced. Each individual filament may consist of a single wire or of strands comprising several joined and preferably twisted together individual wires.

The individual wires may be of identical diameter and/or may have different diameters. The wires may also consist of different materials (nitinol, cobalt-chrome alloys, platinum alloys). Wires made of a radiopaque material, for example, enable the implant to be visible by radiographic methods.

According to the invention the ends of the filaments are, in particular, connected with each other in pairs, where in the case of multiple filaments 'in pairs' means that in each case two bundles of several individual filaments are joined. Such bundles may be of compact arrangement in that all wires are combined into a primarily round bundle and the front ends of all wires are fused together so that a uniform dome-shaped end is produced in this way. In this manner a firmly bonded connection of the individual wires is achieved and the bundle end designed so as to be atraumatic.

Alternatively, the wires may be arranged in parallel with their front ends of fan-shaped configuration being fused together. Advantage of this design is the relative small diameter provided in the connection area in comparison to the filament bundling technique.

Another configuration variant is to group the individual filaments in an offset manner, i.e. the wires are cut to different length so as to be of staggered arrangement. Via its front end face each wire is connected to the adjacent wire. The longest wire can then be used as connecting element. Such a staggered arrangement may be provided both for a fan-shaped and for a compact configuration of the individual wires.

As described hereinbefore, important with the stress-free arrangement of the individual filaments in the braiding is that the implant surface is designed so as to be as dense as possible. Since the flexibility of the braid must be maintained, a 100% coverage of the surface with filaments can at best be approached, however. However, the surface coverage may also be reduced and, depending on the relevant application, such a reduced surface coverage has also proved to be sufficient.

To improve the surface coverage the braid may be coated with a film consisting, for example, of teflon, silicone or other biocompatible plastic material. To increase flexibility and expandibility such a plastic film may be provided with slots which are of staggered arrangement, with the longitudinal direction of the slots extending along the peripheral line of the implant. Such a film may, for example, be achieved by immersing the implant into a suitable liquid film medium (dispersion or solution) and subsequent provision of slots, for instance by means of laser equipment. By immersion the meshes may, for example, be filled fully or partly.

Alternatively, by immersion into a plastic dispersion or solution the individual filaments of the implant may be coated with such a plastic material and the filament cross section increased in this way. In this case the mesh area remains open but the mesh size is significantly reduced.

The implant proposed by the invention is made of customary implant materials having restoring properties, preferably of medical steel having spring characteristics, cobalt-chrome alloys, or of a material with shape-memory properties. In the latter case especially nitinol is considered useful. In any case, it is essential that the implant, on the one hand, is capable of assuming a compressed form so that it can pass through the insertion catheter and, on the other, expands automatically when released from the external force exerted by the insertion catheter and then leans against the inner wall of the vessel at the placement site. The implant can also be manufactured from composite materials, for example using platinum wires coated with nitinol. This enables the shape-memory properties of nitinol to be combined with the radiopacity of platinum.

The implant may be coated in a manner known per se. Suitable coating materials are, in particular, those described for stents, for example materials having antiproliferative, antiphlogistic, antithrombogenous properties or haemocompatible characteristics conducive to ingrowth and/or preventing deposits. Preferred is a coating that promotes the ingrowth of the implant and the formation of neointima. It may be expedient to provide the implant externally with such a type of coating and inside use an agent that inhibits adherence, for example heparin or a derivative, ASS or oligosaccharides and chitin derivatives suitable for the purpose. Further suited in this context are layers of nanoparticles, for example ultra-thin layers of polymeric $SiO_2$ reducing adherence.

According to the invention the filament ends joined with each other may be designed so as form connecting elements. As an example, this may be achieved by arranging slubs/thickenings of defined diameter at these connecting elements, and such slubs may be produced by fusing with the help of laser techniques. Said slubs/thickenings may have a ball-shaped, oval, rectangular, square or similar form and serve the purpose of being held in a form-closed manner by a retaining element attached to a pusher wire before the implant is detached.

Connecting elements may also be arranged at the proximal and/or distal ends of the filaments, with said connecting elements extending further in proximal/distal direction and having ends provided with slubs/thickenings. Said connecting element may be a wire, for instance, which is arranged at the linkage point of two or more filament ends and further extends in axial direction. Slubs/thickenings arranged at the proximal end have special significance in that they are meant in this location to be held by a retaining element in a form-closed fashion. Via the retaining element the implant is coupled to an insertion aid, in particular a pusher or guide wire. During the implant detachment process the form closure between thickening element and retaining element is released causing the implant to be liberated. However, an additional retaining element may also be arranged at the distal end of the implant.

Other than a ball shape the design of the connecting elements may also provide for shapes such as anchors, rectangles or other form pieces. The connecting elements are intended to function according to the key/lock principle, i.e. they interact with a retaining element being provided over its periphery with suitable recesses or receptacles. As long as the retaining element and the implant attached to it in elongated and diameter-reduced form are moved along within a catheter both are mechanically kept bonded together due to the restraint of the catheter wall; and when the retaining element has exited the catheter the implant expands until it reaches its ultimate diameter and in this way disengages itself from the receptacles provided in the retaining element. The attachment and detachment configuration between the connecting elements and the retaining element may also be achieved in some other way. The retaining element is usually of rotationally symmetric design and may, for example, be manufactured of stainless steel or nitinol.

Fixing the implant in the recesses or receptacles of the retaining element may also be brought about by means of a separate hose-like covering drawn over the retaining element so as to achieve a form-closed bond with the connecting elements or connectors being in place in the retaining element. When the implant has reached its ultimate position said covering is retracted and in this manner liberates the implant. Following this, the retaining element with pusher wire, covering and catheter can be retracted. The covering may be a hose of plastic material, a sleeve of plastic or metal, a spiral helix of metal or may also consist of combinations thereof. Securing the covering at the pusher wire to prevent inadvertent displacement can be accomplished by means of a clamping device, for example by a torquer. The covering must not extend over the whole of the pusher wire; it will be sufficient if it reaches over the retaining element and the distal portion of the pusher wire. In this case the covering is retracted via a second wire or thread running parallel to the pusher wire from the covering in proximal direction.

Accordingly, the invention also relates to the combination of an implant of the kind described hereinbefore and a pusher wire to which the implant is attached via the retaining element.

As mentioned above the combination of retaining element and implant is moved through an endovascular catheter. For this purpose, the retaining element may be provided over its periphery with recesses serving to accommodate the connecting elements of the implant. The diameter of the retaining element is to be selected so that it can be passed without difficulty through a catheter of customary design while the connecting elements however being restrained and kept inside the recesses by the inner wall of the catheter. In this context a ball-shaped design of the connecting elements is thought to be of advantage because the faces contacting the inner wall of a customary catheter and thus friction and resistance of the moving components can be minimized.

According to a preferred embodiment slubs/thickenings are arranged at the proximal end of the implant which via form closure are held by the retaining element, wherein a portion of the retaining element is designed so as to be electrolytically corrodible so that the proximal end of the implant is set free when said portion has been dissolved electrolytically. In this case detachment of the implant will not merely be brought about by pushing it out of the catheter or by retracting a covering but it is rather at least necessary that also a portion of the retaining element is subjected to electrolytic corrosion. The corrodible portion in this case is arranged such that it prevents the thickenings projecting into the retaining element from exiting. Said portion may, for example, be a pin arranged between the thickenings and keeping them apart so that the diameter of the implant at the proximal end is too great for the implant to exit from the retaining element. The fixation of the implant at the retaining element via form closure controlled by a portion of the retaining element being designed so as to be electrolytically separable offers special advantages in terms of accurate placement and also, as the case may be, repositioning or retraction of the implant. Nevertheless, a purely electrolytical detachment of the implant from the retaining element as it is known from the state of the art relating to stents and coils is of course also conceivable.

Yet another possibility involves the corrodibly designed portion of the retaining element to be provided in the form of a disk with an opening, wherein the thickenings located at the proximal end of the implant extend through said opening and wherein the diameter of the opening is adapted to the thickenings in such a manner that said thickenings cannot pass through the opening as long as the disk is left intact. Only after the disk has been dissolved at least partially by applying a voltage will the thickenings of the implant be capable of exiting from the retaining element.

For the electrolytically corrodible portion a plurality of materials may be employed which ensure a fast severance and moreover are compatible from a medical viewpoint. Examples are stainless steel, magnesium, magnesium alloys, or cobalt-chrome alloys.

The above described combination involving the form-closed attachment of the implant to the retaining element and the electrolytic dissolution of a portion of the retaining element resulting in the implant to be liberated may also be provided independently of the herein described invention of connecting filaments crossing each other at proximal points of intersection, i.e. with an implant as per the preamble of claim 1. This variant as well is covered by the application.

The retaining element may consist of two fixing elements suitably spaced relative to each other which accommodate the implant restrained between them. In this case both fixing elements are provided with the respective receptacles for the connecting elements of the implant and the implant has been designed to include suitable connecting elements both at its proximal and its distal end.

A suitably designed retaining element with two fixing elements may have both fixing elements connected to one and the same pusher wire at a defined distance so that it is ensured the implant of a given length also undergoes a defined elongation and tensioning. In this manner any excessive elongation is ruled out and the restoring forces that are exerted after the implant is liberated within the vessel can be fully effective. As an alternative the fixing elements may also be attached to two separate pusher wires which enable the implant to be adjusted or elongated by the attending physician or by means of a suitably designed securing device. The second pusher wire may also be designed in the form of a guide tube.

In accordance with another beneficial embodiment of the invention the pusher wire is provided with a pusher wire tip extending from the distal end of the pusher wire further in distal direction and into the inside of the implant, in particular up to the distal end of the implant or even beyond it. It is ensured in this way that even when the implant has been liberated an object still extends through the inside of the implant until the pusher wire is retracted. This makes it possible to probe the vessel respectively implant again, for example by passing a catheter over the pusher wire and ultimately over the pusher wire tip. The catheter is moved in this way through the liberated and expanded implant. Only when the pusher wire is finally retracted will the pusher wire tip be removed.

The pusher wire tip may be designed so as to be rotationally symmetric. Its cross section may be round, oval, rectangular or have another basically optional form. It is moreover considered expedient to visualize the pusher wire tip, for example by manufacturing the pusher wire tip itself at least to some extent of a radiopaque material or by providing the pusher wire tip with a radiopaque marker arranged at the tip's distal end. The pusher wire tip may be manufactured of stainless steel, nitinol, or other metals.

The pusher wire tip and the pusher wire proper may be of one-piece design, in which case the wire fundamentally has a continuous form. However, the pusher wire tip and the pusher wire may as well be separately manufactured and only connected with each other subsequently. In most cases, the diameter of the pusher wire tip will be smaller than that of the pusher wire, i.e. the cross section reduces from the pusher wire towards the pusher wire tip. Furthermore, another advantage of the embodiment is to arrange for the pusher wire tip to have a slightly tapered form, i.e. its diameter reduces towards distal resulting in increased flexibility in distal direction.

The described variant involving the pusher wire tip can also be implemented independently of the herein described invention of connecting filaments crossing each other at proximal points of intersection, i.e. with an implant as per the preamble of claim 1. This variant as well is covered by the application.

The invention is explained in more detail by way of the enclosed figures where

Figure 4:
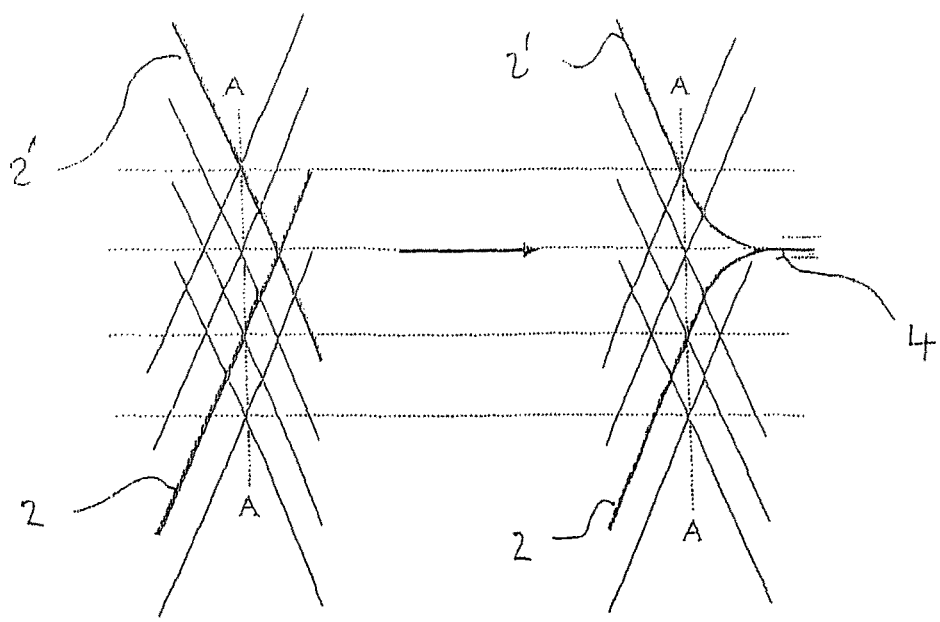
Figure 5:
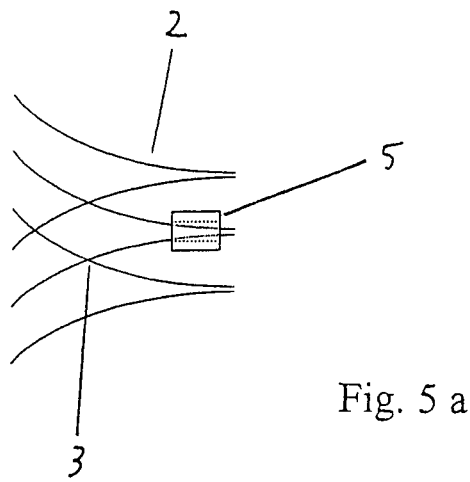
Figure 5:
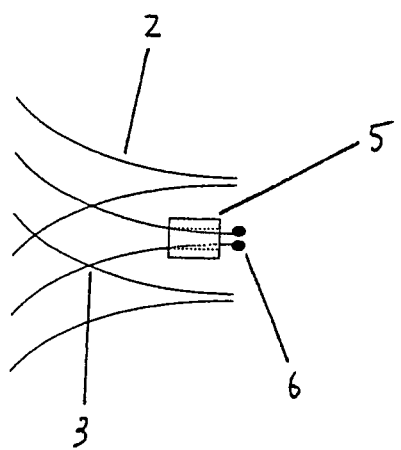
Figure 6:
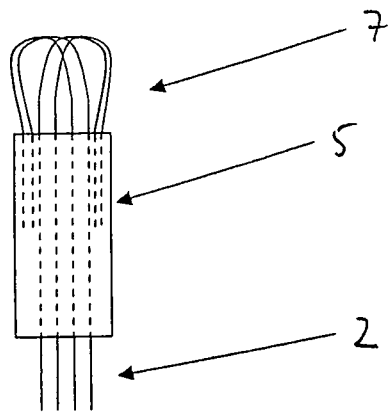
Figure 7:
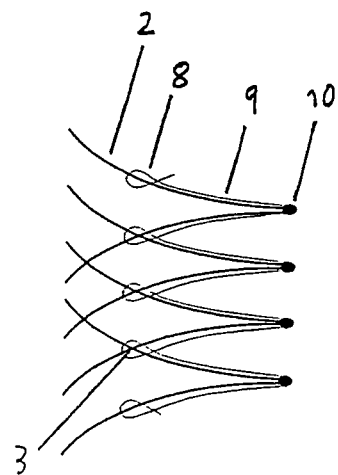
Figure 8:
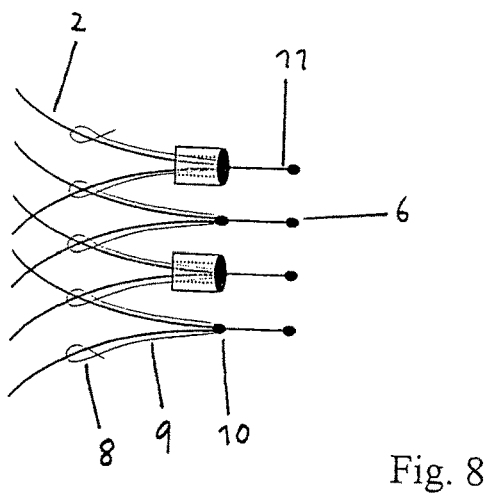
Figure 9:
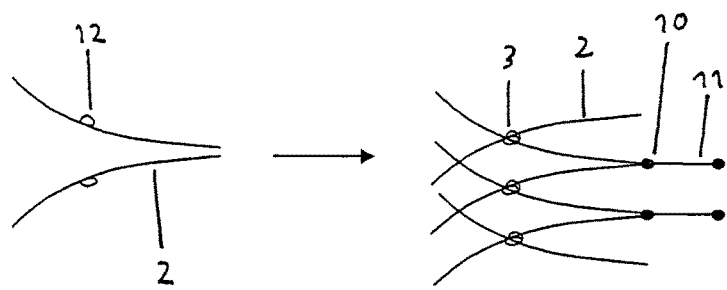
Figure 10:
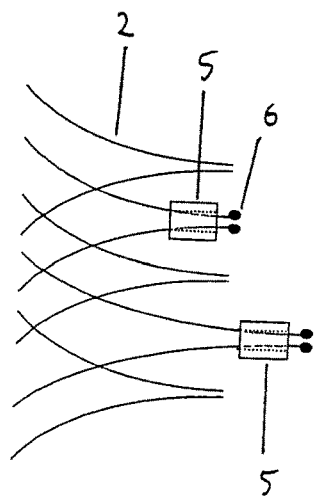
Figure 11:
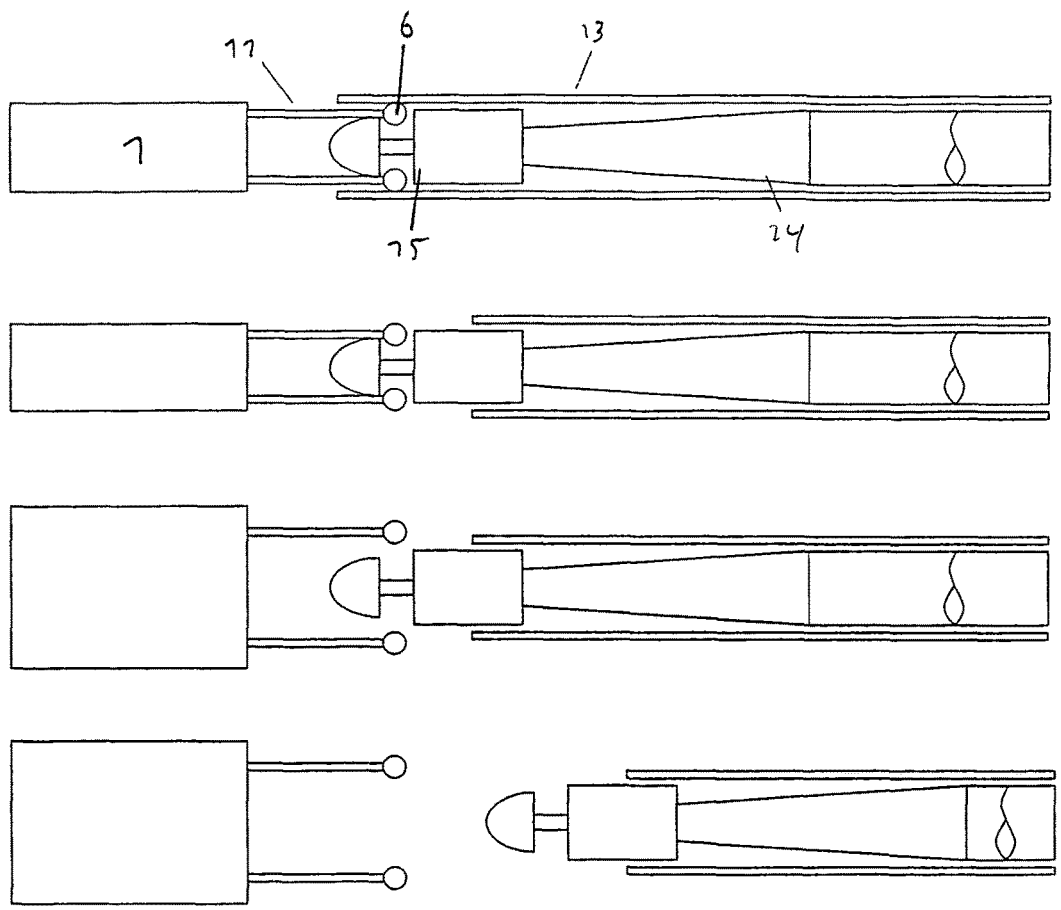
Figure 12:
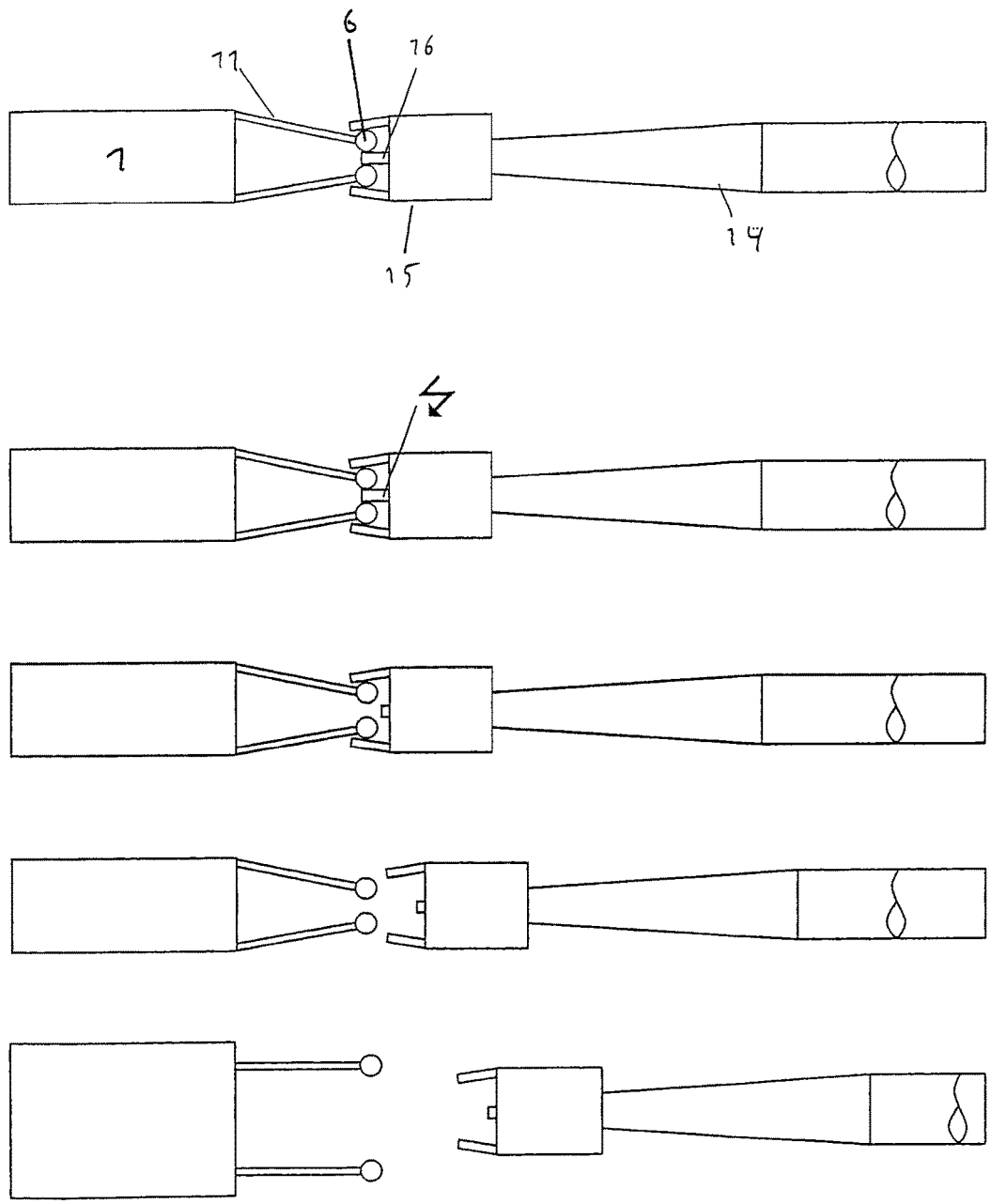
Figure 13:
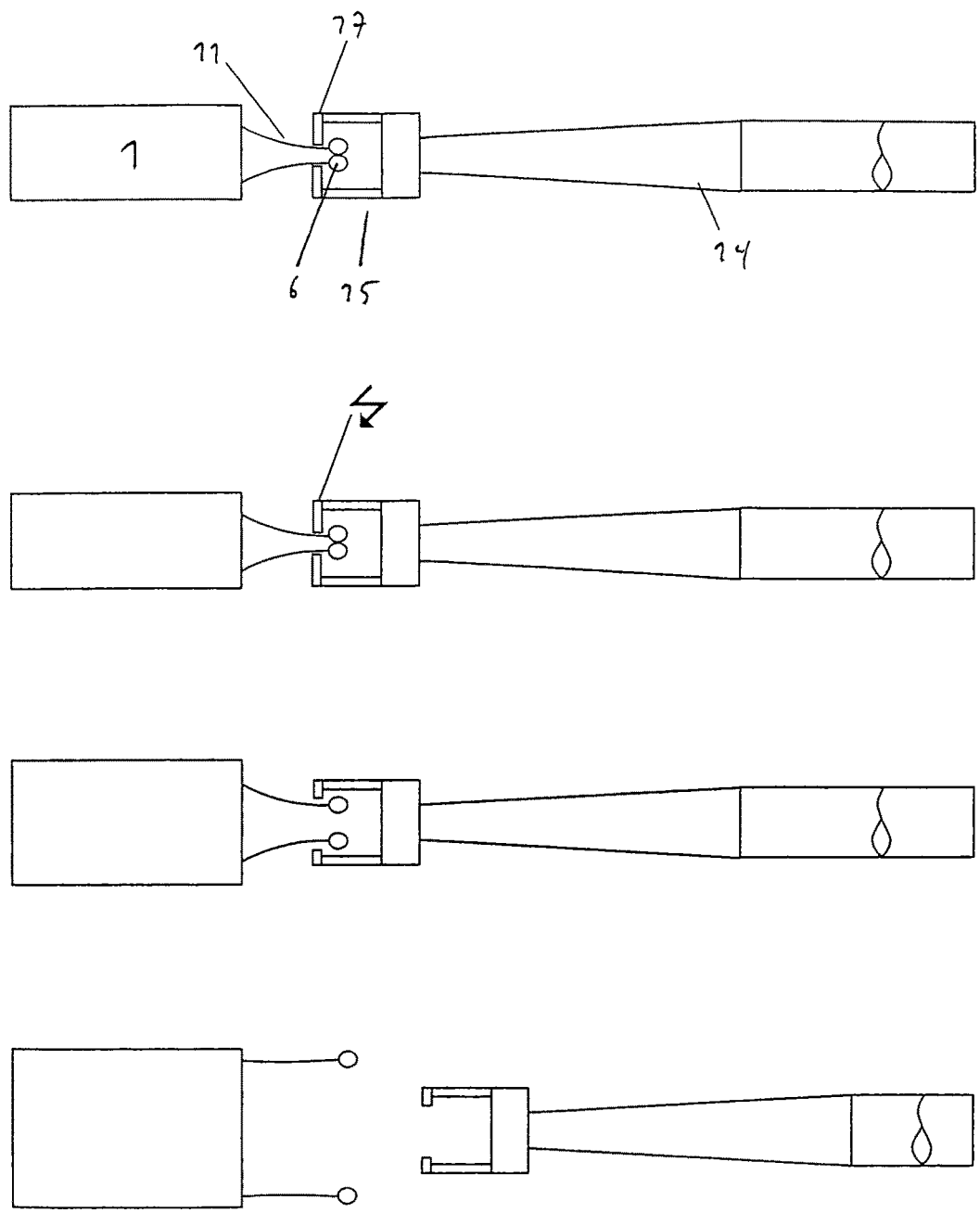
Figure 14:
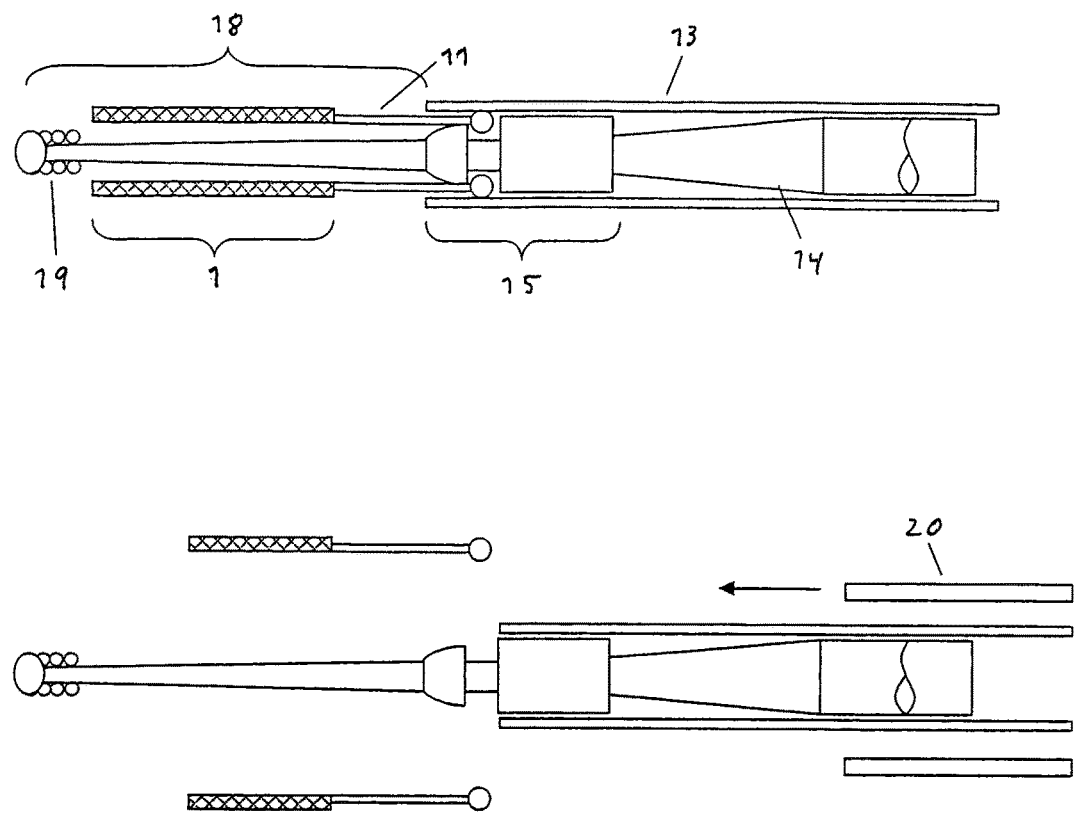

FIG. 4 provides information on how the filament ends of an inventive braiding are joined;

FIG. 5a depicts an alternative embodiment for the connection of filament ends;

FIG. 5b shows the atraumatic design of the filament ends;

FIG. 6 shows another alternative embodiment for the connection of filament ends;

FIG. 7 shows the inventive fixation of the points of intersection;

FIG. 8 illustrates an embodiment with additional connecting elements;

FIG. 9 depicts an alternative embodiment for the fixation of points of intersection;

FIG. 10 shows an embodiment with axially offset sleeves;

FIG. 11 illustrates the fixation of an implant at the retaining element and its liberation;

FIG. 12 shows an alternative way of releasing the implant from the retaining element; and FIG. 13 shows another alternative way of releasing the implant from the retaining element; and FIG. 14 depicts an embodiment with a pusher wire tip extending through the implant.

Figure 1:
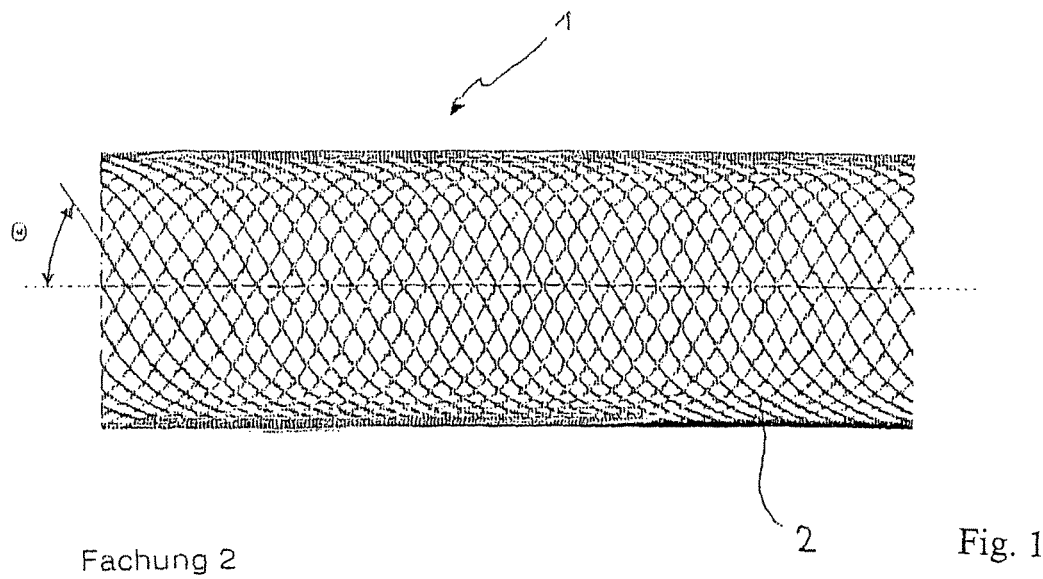
FIG. 1 shows a typical example of a braiding as used in the framework of the invention.

FIG. 1 shows the braid structure of an inventive implant 1 consisting of filaments 2 intertwined with each other. In the example shown the individual filaments intersect at an angle of approx. 120° with the open sides of the angle pointing to the open ends of the braiding. The illustration shows the braid in a slightly stretched/elongated state, i.e. the diameter is reduced.

Angle Theta denotes the braid angle in relation to the longitudinal axis, said angle may amount up to 80° in unstretched condition and at nominal diameter. When the braiding is in elongated position inside the catheter, angle Theta may reduce to approx. 7°.

It is to be understood that the nominal diameter of the braid will match the lumen of the target vessel at the site where treatment takes place.

The braid is manufactured by means of a conventional braiding machine in the form of an endless braid structure. Braiding is performed on a mandrel the external dimensions of which correspond to the inside diameter of the products made with the machine.

The appropriately equipped braiding machine governs the structure of the braid, e.g. the number of threads, the thread run and the number of intersection points over the circumference and per length of lay. The number of threads depends on the number of bobbins, with each of said bobbins revolving halfway around the braiding core in both directions.

The filaments usually consist of metal, for example of steel wire, radiopaque platinum metals or platinum alloys or nitinol. However, plastic filaments of sufficient flexibility may also be used. Ideally, the filament thickness amounts to 0.01 to 0.2 mm, in particular ranges between 0.02 and 0.1 mm. To achieve a high coverage of the wall area flat strip material may be used in lieu of wire material, said flat material being, for example, between 0.05 and 0.5 mm wide, preferably up to 0.1 mm, with the above cited thickness figures.

The inventive braiding can be manufactured using single filaments (plying 1) or two (plying 2) or more individual filaments.

Figure 2:
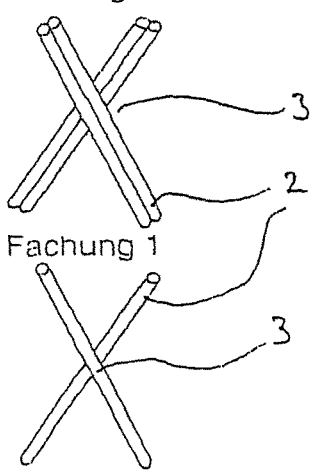
FIG. 2 shows filaments of single or double plying.

FIG. 2 shows points of intersection 3 where two parallelly guided filaments are crossing each other (plying 2) or only single filaments 2 intersect (plying 1). If two or more filaments are put together these will be fed via the same bobbin.

Figure 3:
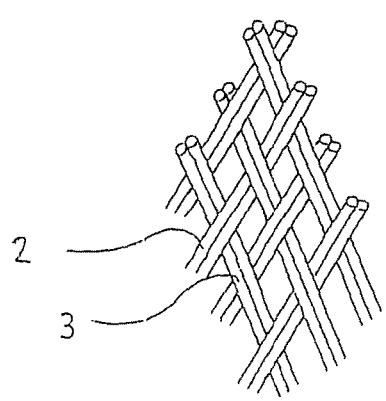
FIG. 3 illustrates a 1-plaited or 2-plaited braiding.
Figure 3:
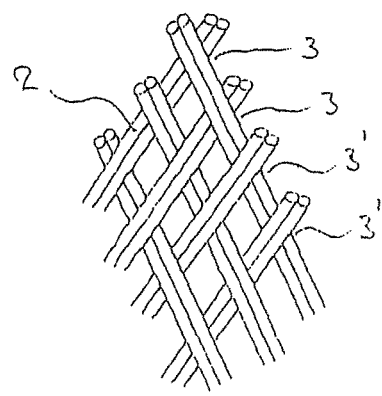

FIG. 3 shows patterns of one-plaited and two-plaited structures formed of filaments 2 of plying 2. In the one-plaited structure the filament pairs are arranged alternating one above the other and one below the other. As can be seen from the illustration, in the two-plaited structure the filament pairs each are extending above two counter-running filament pairs and then underneath two counter-running filament pairs.

A plying of two or an even higher plying configuration results in a higher surface density of the braiding and at the same time reduces the longitudinal expansion when the braiding is compressed. This higher surface density, however, causes flexibility to diminish, also through increased friction and tension. This may be counteracted by making use of a more highly plaited arrangement, i.e. a two-plaited or higher-plaited structure will result in higher flexibility. According to the invention, a two-plaited structure and a plying of 2 are preferred.

After cutting the product to size to yield specific units the braiding ends have to be properly terminated. This is necessary to ensure the form stability of the braided structure and prevent the vascular system from being injured or damaged. Of equal importance in this respect is to provide an orderly structure of the ends of the braid.

FIG. 4 shows how two filaments 2, 2' are combined at the end of the braiding into a filament pair 4, with 2 and 2' being counter-running filaments. For this purpose, the filaments are bent in axial direction and welded together distally. In this manner the filaments positioned one above the other at the marginal points of intersection are connected to each other. For example, such points of intersection are located along line A-A.

FIG. 5a illustrates how the ends of filaments 2 are held together by a sleeve 5. Sleeve 5 may be attached to the filaments by welding or crimping. Moreover, sleeve 5 may at the same time serve to visualize the implantation process provided the sleeve consists of a material which is radiopaque/impenetrable by x-rays.

As can be seen from FIG. 5b the filament ends may be provided with atraumatic clubs/thickenings 6. These may be formed out of the filament 2 or attached additionally. If thickenings 6 are of sufficient diameter this alone will prevent sleeve 5 from sliding off the filament ends. However, sleeve 5 may of course also retained/secured by crimping, welding, soldering, adhesive bonding or the like. FIGS. 5a,b show the distal end of an implant 1, but a similar filament fixation method can be adopted at the proximal end as well.

The fixation of the ends of filaments 2 by means of a sleeve 5, in particular at the distal end, is shown also in FIG. 6. However, other than in the example illustrated before, the ends of the filaments in this case are run back into sleeve 5 such that a loop 7 is formed. Also in this way an atraumatic end can be created.

In FIG. 7 the central idea of the invention has been illustrated, which is the fixation of filaments 2 crossing each other at the proximal point of intersection 3. This is achieved by placing a loop 8 around the point of intersection 3. Said loop 8 is formed by wire 9 which in turn is secured at the proximal end 10 of the implant 1. So when the implant 1 is expanding, a displacement of the points of intersection 3 located farthest towards the proximal end is prevented in this manner which ensures maximum implant widening without individual filaments 2 projecting into the inside of the vessel lumen.

In FIG. 8 the embodiment shown in FIG. 7 has been supplemented by additional sleeves 5, wherein sleeves 5 in this case are only attached to some of the filament ends. Sleeves 5 in this case serve marking purposes and are manufactured from a radiopaque material to allow the implant 1 to be placed in position under radiographic control.

Additionally, in FIG. 8 connecting elements 11 arranged at the proximal end of the implant 1 are shown, said connecting elements being provided with thickenings 6 at their proximal end. These thickenings 6 are suitably designed so as to engage in a retaining element 15 which governs the release of the implant 1.

FIG. 9 shows an alternative way of connecting the filaments 2 with each other in the area of the proximal points of intersection 3. In the area of proximal points of intersection the filaments are provided with eyelets 12. Filament 2 that crosses filament 2 in this area, with the latter being provided with eyelet 12, passes through this eyelet 12, wherein this filament 2 also has been designed so as to have an eyelet 12 to restrain its longitudinal movability in this location. In this case, the means by means of which the filaments 2 are secured form part of said filaments 2.

In FIG. 10 the proximal or distal end of an implant 1 is illustrated, wherein sleeves 5 being placed on the filament bundles as radiopaque markers. Sleeves 5 are arranged to some extent axially staggered. By this arrangement the amount of radial expansion of implant 1 in compressed condition can be kept small, i.e. the height of profile is lower than if all sleeves 5 were located in the same axial position.

FIG. 11 shows the fixation and detachment of implant 1 connected to pusher wire 14 via a retaining element 15. Retaining element 15 and pusher wire 14 are ensheathed in a hose-like covering 13. Retaining element 15 is provided with recesses which accommodate the thickenings 6 at the proximal end of implant 1. As long as the retaining element encloses covering 13 the thickening elements 6 are prevented from exiting the retaining element 15. However, retracting the covering 13 permits implant 1 to expand at the proximal end so that the thickenings disengage from retaining element 15 and are set free. Subsequently, the pusher wire 14 to which distal end the retaining element 15 is attached can also be retracted.

An alternative embodiment involving the detachment of the implant 1 from retaining element 15 is depicted in FIG. 12, wherein said embodiment, although also having thickenings 6 arranged at the connecting elements and engaging in suitable recesses of the retaining element 15, provides for the release not being effected via the retraction of a covering but rather by eliminating the electrolytically corrodible portion 16 by applying an electrical voltage, indicated in the figure by a lightning symbol. Before it is eliminated/dissolved this portion 16 prevents thickenings 6 from disengaging from the retaining element. When it has been dissolved, however, adequate room is available so that a detachment and expansion of implant 1 can take place. Combining a form-closed fixation of implant 1 at the retaining element 15 with an electrolytically effected detachment functionality enables an additional covering or sheathing of the retaining element 15 to be dispensed with.

Another alternative way of achieving an electrolytical detachment is shown in FIG. 13. Thickenings 6 are held in position in retaining element 15 in a form-closed manner, with a disk 17 with centrically arranged opening in this case preventing thickenings 6 from exiting. Said opening has a diameter that although it allows the passage of the connecting elements 11, prevents thickenings 6 at the proximal end of the connecting elements 11 from moving through said opening. However, as soon as disk 17 has been dissolved electrolytically detachment and expansion of implant 1 can take place. Subsequently, the pusher wire 14 with retaining element 15 is retracted.

In FIG. 14 an embodiment of the invention is illustrated wherein a pusher wire portion, that is to say the pusher wire tip 18 distally arranged on the pusher wire 14 extends through the interior of the implant 1. The pusher wire tip 18 extends through the entire implant 1 and terminates at the distal end in marker 19 made of radiopaque material which in this case is designed in the form of a marker coil. The pusher wire tip 18 is thinner than the pusher wire 14 proper and is of tapered configuration in distal direction which not only ensures that the interior of implant 1 is large enough to accommodate the pusher wire tip 18 also in compressed form but that also the flexibility increases towards distal.

Retracting the covering 13 enables implant 1 to be released as described in connection with FIG. 11 so that the implant 1 is free to expand. However, the pusher wire tip 18 still extends through the interior of the implant 1 until the pusher wire 14 has been retracted. Due to the expansion of the implant 1 and its shortening thus caused the pusher wire tip 18 still projects beyond the distal end of the released implant 1 slightly more than before. At this time and when thought expedient by the attending physician a catheter 20 may be pushed over the pusher wire 14 and the pusher wire tip 18 through the implant 1, as indicated in the figure by an arrow.

The invention claimed is:

1. An implant for blood vessels to influence the flow of blood in an implantation site comprising the area of arteriovenous malformations, said implant having proximal and distal ends and a wall comprising individual filaments forming a tubular braiding extending in axial direction from the proximal to the distal end, wherein
the individual filaments have ends at the proximal and/or distal end of the braiding and cross one another to form points of intersection, and wherein
the implant is deformable in such a manner that, when accommodated in an insertion catheter, it is shaped so that its diameter is reduced and can be expanded at the implantation site and adapt to the diameter of the blood vessel into which it is inserted, and wherein
the filament ends at the proximal and/or distal end of the braiding are each brought together at least in pairs and connected with each other permanently, and
with the filament ends connected with each other being shaped so as to be atraumatic, characterized in that
the filaments crossing one another at the points of intersection located distally from the proximal ends are connected with each other at said points of intersection in the area of the proximal end of the implant, in the following manner:
the intersected filaments in the area of the proximal end of the implant are passed through loops formed by wires secured at the proximal end of the implant, the wires originating from the points where the filaments are brought together at the proximal end of the implant, the starting point and the end point of the wires being at the proximal end of the implant, the individual wires extending from the proximal point of attachment in distal direction and passed around the proximal points of intersection of the filaments.

2. An implant according to claim 1, characterized in that the filaments crossing each other are connected with each other at points of intersection located farthest to the proximal end and distally to the filament ends.

3. An implant according to claim 1, characterized in that radiopaque markings are arranged at the ends of the filaments brought together at the proximal and/or distal end of the implant.

4. An implant according to claim 3, characterized in that the radiopaque markers are sleeves surrounding the joined filaments.

5. An implant according to claim 4, characterized in that the sleeves surrounding the joined filaments located adjacent to one another are of staggered arrangement with respect to each other in axial direction.

6. An implant according to claim 1, characterized in that the filaments are metallic individual wires or strands.

7. An implant according to claim 1, characterized in that connecting elements are arranged at the proximal and/or distal filament ends, with said connecting elements extending in proximal or distal direction and being provided with thickenings at their ends.

8. A combination comprising an implant according to claim 1 and a pusher wire, wherein the implant is attached to the pusher wire via a retaining element.

9. A combination according to claim 8, characterized in that thickenings are arranged at the proximal end of the implant which are held in a form-closed manner by the retaining element, wherein a portion of the retaining element is designed so as to be electrolytically corrodible so that the proximal end of the implant is set free when said portion has been dissolved electrolytically.

10. A combination according to claim 9, characterized in that the corrodibly designed portion of the retaining element is provided in the form of a disk with an opening, wherein the thickenings located at the proximal end of the implant extend through said opening and wherein the diameter of the opening is adapted to the thickenings in such a manner that said thickenings cannot pass through the opening as long as the disk is left intact.

11. A combination according to claim 8, characterized in that the pusher wire is provided with a pusher wire tip extending from the distal end of the pusher wire further in direction of the distal end of the implant and into the interior of the implant up to the distal end of the implant or even beyond it.

* * * * *